United States Patent
Crafton

(10) Patent No.: US 12,310,882 B2
(45) Date of Patent: *May 27, 2025

(54) HANNAH CERVICAL CUP

(71) Applicant: Ashley Camille Crafton, Apo (DE)

(72) Inventor: Ashley Camille Crafton, Apo (DE)

(*) Notice: Subject to any disclaimer, the term of this patent is extended or adjusted under 35 U.S.C. 154(b) by 752 days.

This patent is subject to a terminal disclaimer.

(21) Appl. No.: 17/681,781

(22) Filed: Feb. 27, 2022

(65) Prior Publication Data

US 2022/0175573 A1    Jun. 9, 2022

Related U.S. Application Data

(63) Continuation of application No. 17/047,147, filed as application No. PCT/US2019/032542 on May 16, 2019, now Pat. No. 11,311,409.

(60) Provisional application No. 62/673,872, filed on May 19, 2018.

(51) Int. Cl.
| | |
|---|---|
| *A61F 6/12* | (2006.01) |
| *A61B 17/42* | (2006.01) |
| *A61B 90/00* | (2016.01) |

(52) U.S. Cl.
CPC ................ *A61F 6/12* (2013.01); *A61B 17/42* (2013.01); *A61B 90/03* (2016.02); *A61B 90/08* (2016.02); *A61B 2090/032* (2016.02); *A61B 2090/0807* (2016.02)

(58) Field of Classification Search
CPC . A61F 6/12; A61F 6/146; A61B 17/42; A61B 17/44; A61B 17/442; A61B 17/4241; A61B 17/12; A61B 17/12009; A61B 17/12013; A61B 2017/4225
See application file for complete search history.

(56) References Cited

U.S. PATENT DOCUMENTS

| | | | |
|---|---|---|---|
| 1,991,278 | A | 2/1935 | Heintz et al. |
| 2,818,856 | A | 1/1958 | Kohl |
| 3,765,408 | A | 10/1973 | Kawai |
| 4,517,970 | A | 5/1985 | Goepp et al. |
| 5,065,772 | A | 11/1991 | Cox |
| 5,928,249 | A | 7/1999 | Saadat |
| 7,165,550 | B1 | 1/2007 | Tracy et al. |
| 9,474,885 | B2 | 10/2016 | Cline |
| 10,499,926 | B2 | 12/2019 | Tour et al. |

(Continued)

FOREIGN PATENT DOCUMENTS

| | | |
|---|---|---|
| CN | 114129862 | 3/2022 |
| KR | 101796393 B1 | 11/2017 |
| WO | 2010114577 A1 | 10/2010 |

OTHER PUBLICATIONS

International Search Report and written opinion issued on Jul. 29, 2019 on the related International Application of No. PCT/US2019/032542 filed internationally on May 16, 2019.

(Continued)

*Primary Examiner* — Carrie R Dorna
(74) *Attorney, Agent, or Firm* — Mardson Q McQuay

(57) ABSTRACT

A cervical cup includes a body having a flange and a vacuum port so that application of a vacuum to the port will secure the cervical cup to a cervix disposed inside of the body of the cup. Example of the disclosed methodology to treat preterm birth includes inserting of a cervix into a cervical cup and applying a vacuum to a vacuum port of the cervical cup so as to secure the cervical cup to the cervix.

20 Claims, 17 Drawing Sheets

(56) References Cited

U.S. PATENT DOCUMENTS

| | | |
|---|---|---|
| 11,311,409 B2 | 4/2022 | Crafton |
| 11,607,248 B1 | 3/2023 | Booher, Sr. |
| 2012/0283595 A1 | 11/2012 | Curtis et al. |
| 2013/0276792 A1 | 10/2013 | Moch |
| 2015/0265456 A1 | 9/2015 | Booher, Sr. |
| 2016/0250229 A1 | 9/2016 | Campos Perez |
| 2017/0087344 A1 | 3/2017 | Ichim |
| 2019/0008674 A1 | 1/2019 | Myers |
| 2019/0183530 A1 | 6/2019 | Yang et al. |
| 2019/0282350 A1* | 9/2019 | Conti .................... A61F 6/12 |
| 2021/0338474 A1 | 11/2021 | Mamo et al. |
| 2022/0022916 A1 | 1/2022 | Uchida et al. |

OTHER PUBLICATIONS

V. Tsatsaris et al, "Balloon Replacement of Fetal Membranes to Facilitate Emergency Cervical Cerclage," The American College of Obstetricians and Gynecologists, vol. 98 No. Aug. 2, 2001.

A.H. Shaaban and A. Ma. "Cervical pessary for preventing preterm birth," Cochrane Database of Systematic Reviews 2013, Issue 5. DOI: 10.1002/14651858.CD007873.pub3.

D. Vaitkaine and S. Bergstrom, Management of Amniocentisis in Women with Oligohydamnios due to Membrane Rupture: Evaluation of a Cervical Adapter, Gynecol Obstet Invest, 1995; 40:28-31.

International Search Report and written opinion issued on Sep. 4, 2024 on the related International Application of No. PCT/US2024/027949 filed internationally on May 6, 2024ß.

\* cited by examiner

HANNAH CERVICAL CUP

CROSS REFERENCE TO RELATED APPLICATIONS

This application claims priority to U.S. patent application Ser. No. 17/047,147, filed on Oct. 13, 2020, which claims priority to the PCT application with reference number PCT/US2019/032542, filed on May 16, 2019, which claims priority to U.S. patent application Ser. No. 62/673,872, filed on May 19, 2018, entitled "Hannah Cervical Cup," the contents of which are all herein incorporated by reference in their entirety.

BACKGROUND

Technical Field

Embodiments of the subject matter disclosed herein relate generally to apparatuses, methods and systems and, more particularly, to devices, processes, mechanisms and techniques for the treatment of preterm births.

Description of Related Art

Every year, an estimated fifteen million babies are born preterm (before 37 completed weeks of gestation), and this number is rising. Preterm birth complications are the leading cause of death among children under five years of age and responsible for approximately one million deaths in 2015. Those that survive often suffer from debilitating disabilities such as developmental, learning, visual, and hearing impairments. Across the world, the rate of preterm birth ranges from 5% to 18% of all births. Experts have declared that preterm birth is in quantity and severity the most important contributor of perinatal morbidity and mortality both in well- and low-resource countries and, of course, is impacting the health of families around the globe. Preterm birth happens for many known and unknown reasons.

One complication that leads to preterm birth is cervical insufficiency (a medical condition of pregnancy in which the cervix begins to dilate (open) and efface (thin) in the absence of contractions, thus the cervix cannot retain the pregnancy to full term). The cause for cervical insufficiency is unknown, although it is thought to be multifactorial and different for every woman. Currently, there are three main methods of treatment for cervical insufficiency: cerclage, progesterone supplementation, and pessary application.

Cervical cerclage refers to a variety of procedures that use sutures or synthetic tape to reinforce the cervix during pregnancy with women who have a history of a short cervix or cervical insufficiency in a prior pregnancy, or with women who present with a short cervix (a "rescue" cerclage). There are several different techniques to cerclage placement, but the general idea is that non-absorbable suture is placed during surgery to tie closed the cervix. Cervical cerclage can be done through the vagina (transvaginal cervical cerclage) or, less commonly, through the abdomen (transabdominal cervical cerclage). They can be placed pre-conceptually, after conception, or as a "rescue" cerclage (after pregnancy has begun and the discovery of an insufficiency has been made). This approach increases the neonatal survival rate from 43% to 71% and typically increases the gestational age at delivery from 25 to 30 weeks. Unfortunately, cerclages have many drawbacks. Transvaginal cerclages have the drawback of not pulling uniformly on the cervix and having the risk of "tearing through" the cervix and can undermine the integrity of the already weakened cervix. Transabdominal cerclages have proven to be more effective, but, given their more invasive nature, are almost impossible to place after pregnancy has been established, therefore cannot be used as a type of rescue cerclage and must be placed only for patients who have a historical diagnosis. Cerclages have proven to be non-effective in multiple gestational pregnancies, are invasive, and must be placed under the presence of anesthesia.

Progesterone supplementation, which can be performed via weekly intramuscular injections or per regular vaginal suppository, is by itself controversial and its efficacy has been debated. A recent study found that this treatment is not beneficial, suggesting that the role of progesterone may be more limited than previously thought.

A pessary is an apparatus (a ring-like device) that is inserted into the vagina to reduce the protrusion of pelvic structures into the vagina by the application of a localized positive pressure on the cervix. Pessaries are of varying shapes and sizes. One traditional pessary type is the Arabin pessary that was first produced and used in the 1970's in Germany. Several other types of pessary have been used in an attempt to prevent preterm birth, but none have been very successful. The Arabin pessary has mixed literature also regarding its efficacy of use and therefore is not a common treatment for cervical insufficiency in the United States. Most practitioners use a combination of therapies to treat cervical insufficiency. Even a combination of therapies has proven to be controversial as well, as no randomized trials have evaluated the efficacy of a combination therapy.

Another complication that leads to preterm birth is Pre-term Pre-labor Rupture Of Membranes (PPROM). PPROM is the spontaneous or iatrogenic rupture of the fetal amnion ("water breaking") prior to the fetus reaching full gestation that is unaccompanied by contractions. PPROM is responsible for, or associated with, approximately one-third of preterm births and the single most common identifiable factor associated with preterm delivery. The treatment for PPROM is less straight forward than its diagnosis and is a source of controversy throughout perinatal medicine. The treatment of PPROM depends on many factors, including whether or not the patient is (1) showing signs of infection (fever, increase in leukocytes, septicemia, purulent vaginal drainage, etc.); (2) at risk for a prolapsed umbilical cord and/or placental abruption; or (3) mother or fetus are showing signs of distress. However, PPROM is strongly associated with oligohydramnios (little amniotic fluid) and anhydramnios (no amniotic fluid) and early, sever, prolonged oligohydramnios [and anhydramnios] can be associated with pulmonary hypoplasia, facial deformation, and orthopedic abnormalities. Each day and week that passes, the risks and benefits of prolonging the pregnancy must be weighed and the plan of care adapted accordingly.

Administration of corticosteroids is one treatment option for PPROM. These drugs benefit the fetus as they encourage early fetal lung development, but they can hinder the prolongation of the pregnancy as they decrease the dyad's ability to fight infection and, as the uterus is now a new ideal pathway for infection, puts both mother and fetus at greater risk. Another treatment option includes the administration of prophylactic antibiotics and, if needed, tocolytics (medications used to suppress contraction). Tocolytics typically used include terbutaline, indomethacin, nifedipine, and/or magnesium sulfate. These are all controversial due to off-label use, lack of efficacy and, at the same time, are all the standard-of-care. Expectant management usually includes at least some initial hospitalization and often hospitalization until delivery in order to manage effectively the timely assessments and care of mother and fetus which include, but are not limited to, frequent vital sign assessments and fetal heart rate assessments. Hospitalization can also assist in helping to limit the outside activities of the mother (such as work, family, and household duties), thereby mitigating risks associated with such tasks. Most practitioners use a combination of such treatments to address the diagnosis of PPROM.

Another complication that leads to preterm birth is preterm labor. Preterm labor is the presence of uterine contractions that leads to cervical change prior to 37 completed weeks of gestation. Preterm labor is another difficult phenomenon to diagnose and its cause is unknown, but is probably multifactorial and different for every woman. Some women with this diagnosis deliver preterm and some are able to carry the pregnancy to term. Data on the number of women who are diagnosed with preterm labor and continue the pregnancy until term are unclear. Usual treatment includes all treatments mentioned previously for both cervical insufficiency and PPROM and can include progesterone supplementation, pessary use, corticosteroids, tocolytics, intravenous hydration, treatment of underlying infections, bedrest, and hospitalization. Treatment for these patients proves difficult because of the aforementioned problems, but also because many tocolytics are not proven to be effective or beneficial to both maternal and neonatal outcomes.

However, despite the above-summarized progress in treating preterm birth to date no devices, processes, and/or methods exist that are capable of treating these conditions without undermining the integrity of an already weakened cervix, being so invasive in nature, being more effective in multiple gestational pregnancies, unnecessarily exposing mother and baby to prolonged use of controversial (often times off-label) drugs of at least questionable efficacy, reducing the need of hospitalization during treatment, or reducing the risk of infections.

SUMMARY

One or more of the above-summarized needs or others known in the art are addressed by apparatuses, methods, and processes to treat preterm births. As disclosed herein, such apparatuses include a cervical cup having a body, a flange attached to the body at one of its end portions and a vacuum port disposed at the other end portion of the body so that application of a vacuum to the vacuum port will secure the cervical cup to a cervix disposed inside of the body.

Methods for treating preterm births include inserting end portions of a cervix into a body of a cervical cup having a flange and a vacuum port and applying a vacuum to the vacuum port so as to secure the cervical cup to the cervix disposed inside of the body.

BRIEF DESCRIPTION OF THE DRAWINGS

The accompanying drawings (not drawn to scale), which are incorporated in and constitute a part of the specification, illustrate one or more embodiments and, together with the description, explain these embodiments. In the drawings.

DETAILED DESCRIPTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of apparatuses, systems, or methods for treating preterm births.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures, or characteristics may be combined in any suitable manner in one or more embodiments.

Figure 1:
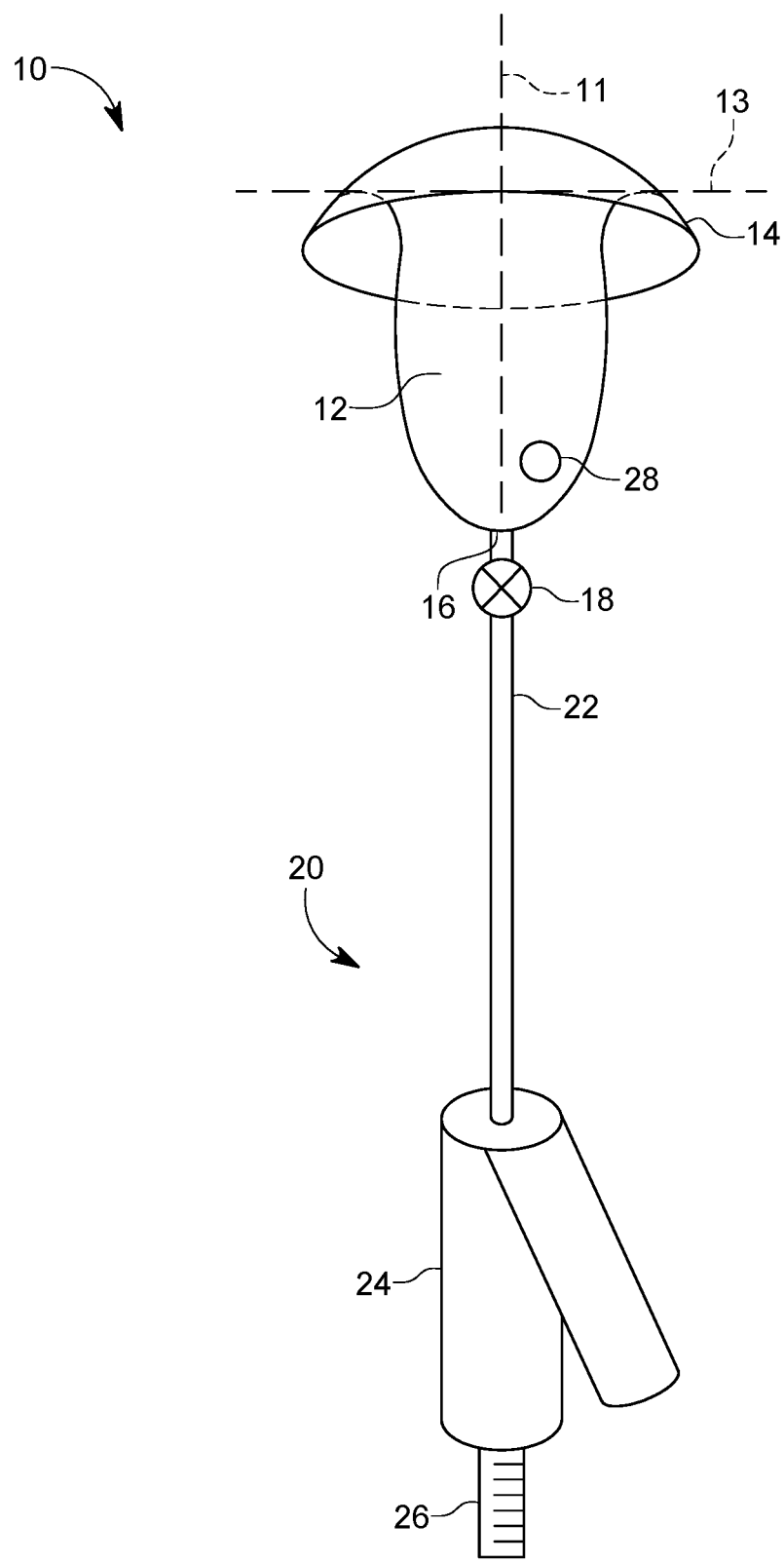
FIG. 1 illustrates an exemplary embodiment of a cervical cup and an applicator according to one aspect of the subject matter disclosed.

FIG. 1 illustrates an exemplary embodiment of a cervical cup system 10 according to one aspect of the subject matter disclosed. As illustrated, the cervical cup system 10 comprises a cervical cup 12 having an inverted flange 14 and a connecting or vacuum port 16 so as to allow the connection of an applicator 20 as illustrated. The cervical cup 12 is shaped in the general form of a cervix, similar to a cervical cap, a menstruation cup, or a diaphragm. The main body of the cervical cup 12 extends generally along an axial axis 11 with the inverted flange 14 generally disposed around a radial axis 13, as shown in FIG. 1. In the illustrated exemplary embodiment, the applicator 20 includes a stem or tube 22 connecting a vacuum-generating device or source 24 to the connecting port 16 of the cervical cup 12. A vacuum gage 26 can also be part of the applicator 20 so as to facilitate the application of the cervical cup 12 to the cervix of a pregnant woman as illustrated in FIG. 2.

Figure 2:
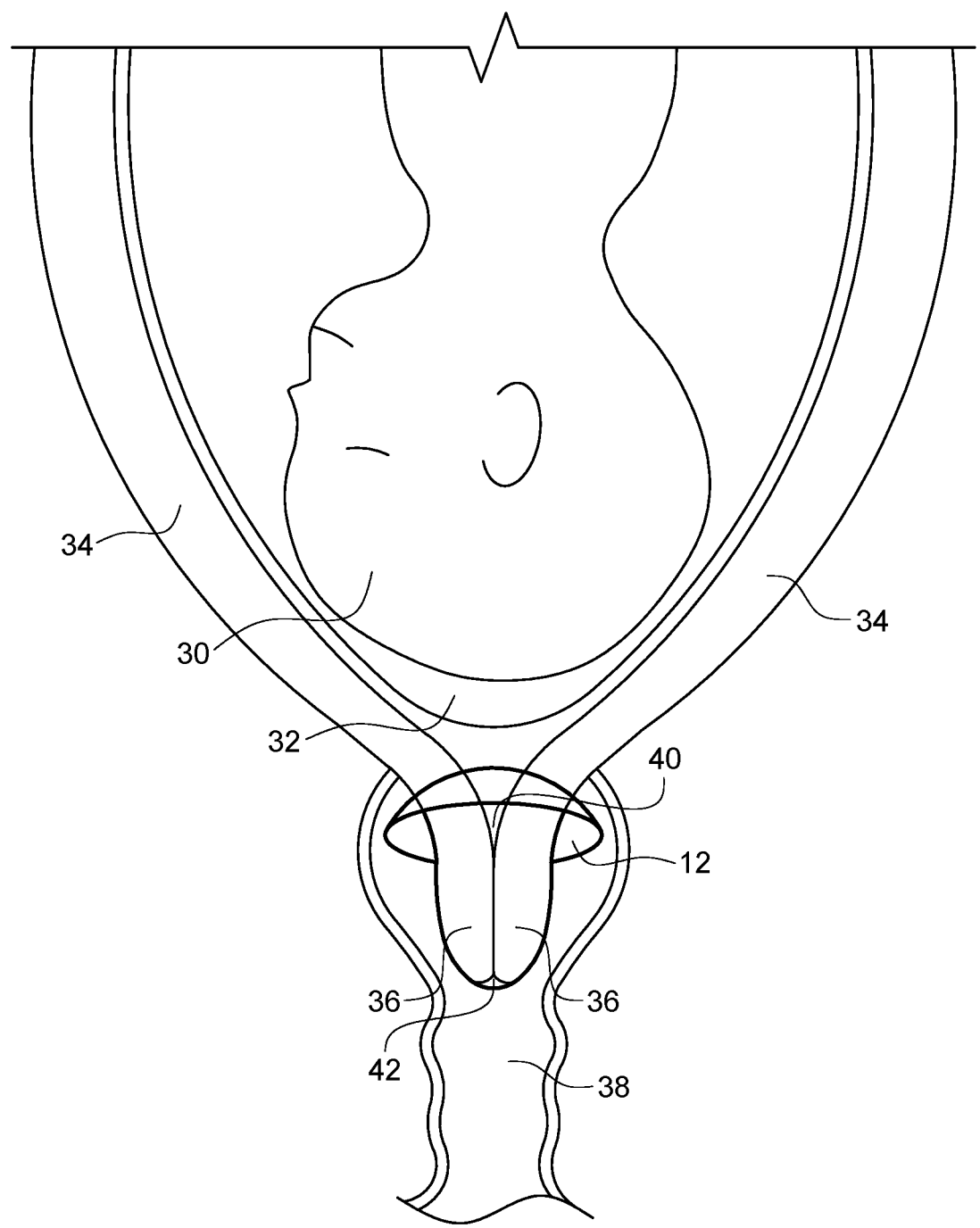
FIG. 2 illustrated the placement of the cervical cup of FIG. 1 on a pregnant woman.

FIG. 2 illustrated a fetus 30 surrounded by an amnion 32 contained by a uterine wall 34 with a cervix 36 forming the closure of the uterine wall 34 inside a vagina 38. As shown, the cervical cup 12, when applied, helps the cervix 36 to remain closed, thick and high, thus allowing the pregnancy to be extended in the face of the above-noted challenges, including cervical insufficiency, PPROM, and preterm labor. Inner and outer (40 and 42) ora at either end of the cervix are internal (to the uterus) or external (to the vagina) openings of the uterine wall 34. One of advantageous benefits of the cervical cup 12 is that its use will prolong pregnancy. The prolongation of pregnancy for many women will mean a reduction in deaths, problems, and healthcare costs associated with neonatal and long-term healthcare.

Those of ordinary skill will also appreciate that the size and shape of the cervical cup 12 may vary and will depend on many factors such as whether or not the woman is pregnant for the first time, how far along in the pregnancy, the current health of the cervix, any history of cervical procedures (such as Loop Electrical Excision Procedure (LEEP), cryotherapy, or cone biopsy), the woman's own anatomical variances, and other factors. Typically, an inner diameter of the cervix cup 12 can vary approximately from 4 to 6 cm and the length of the cup may be approximately 7 cm long. However, those of ordinary skill will understand that the physical size and shape of the cervical cups being disclosed herein should in no way limit the subject matter claimed.

The cervical cup 12 is designed to encourage cervical maintenance, elongation, and constriction and can be attached to the applicator 20 in order to assist in introducing the device into the vagina and to attach it to the cervix or the same may be placed via digital exam. The applicator 20 can be made of many different types of material, including but not limited to polymeric materials, plastic, silicone, latex, rubber, metals, etc. The applicator 20 can be non-flexible or flexible. Embodiments using a flexible applicator may optionally include a guide wire or stylet for added stability.

In certain embodiments, a system is provided to facilitate removal of the applicator 20 from the vagina following cup placement while leaving the cup in place. Applicability of such a system would depend on the system used for maintenance, constriction, and elongation. For example, if a vacuum system is in use this applicator removal system would need to include a way to cut off the vacuum source 20 while maintaining the negative pressure applied to the cervix 36 such as a cap, a clip, a band, a zip-tie, and a plug (generally illustrated as element 18 in FIG. 1). In other embodiments, the use of surgical glue or a tape (applied either during the manufacturing process of the cervical cup or before its placement on a pregnant women by a practitioner) will assist with the placement of the cervical cup 12 for extended periods of time.

Cervical dilation and effacement/shortening happens for two main reasons—chemical changes and mechanics of labor—and the solutions proposed herein address both of these reasons. Furthermore, the subject matter being disclosed also has the ability to address hormone changes pharmaceutically as will be discussed.

One of the few treatments of a mechanical nature—the Arabin pessary—has not proven to be an efficacious way of preventing preterm birth in the general population. There has been some research performed, though, on the mechanisms of action at work in those for whom it is effective. This research has shown that the change in the uterocervical angle towards the posterior position, development of cervical edema, and restoration of endocervical length may be the mechanisms of action that prevent preterm birth in some women. The cervical cups disclosed herein accomplish the same positive results without exerting a compressive (positive) pressure on the cervix. It has been shown that positive pressure on the cervix promotes dilation and effacement, as demonstrated by the cervical ripening that occurs during the use of a double lumen cervical ripening catheter. Such catheters produce positive pressure on the cervix by filling two balloon cavities with water that press on the cervix, causing both dilation and effacement—a result contrary to the desired outcome when treating preterm births and their associated complications.

One of the inventive aspects of the subject matter being disclosed is the application of negative pressure to a dilated and/or effaced cervix so as to mechanically constrict the cervical os and to cause it to elongate and preserve the thickness and closure that the cervix is already maintaining, either prophylactically early on in pregnancy or salvifically when a patient is experiencing symptoms that may lead to preterm delivery. Application of this type of cup via suction to a closed and thick cervix as well, will then add strength and constitution to the cervix in a way not seen in alternate methods to treat preterm births, leading to preservation of cervical closure and length, and possibly even elongation and constriction of the cervical os.

Therefore, considering the nature of the cervical tissue (a buttery-like substance), the application of a positive pressure (compressive stress) by conventional devices pushes the cervical tissue and "dissolves" it so as to induce labor. The cervical cup 12 (and its many variations that will be further described herein) will do the opposite. Application of a gentle negative pressure (tensile stress) on the cervix will keep it in place delaying labor. Pessaries normally surround the cervix on the outside to support any pressure of the baby head coming down. Pessaries are not glued in place and sometimes come out.

Occasionally, as a woman labors, the cervix begins to become edematous due to many factors such as cephalopelvic disproportion or asynclitic presentation of the fetus. This edema leads to added elongation of the cervix and constriction of the cervical ora and often halts the progress of labor despite contractions. The subject matter disclosed herein mimics this phenomenon by the application of a vacuum, allowing gentle suction (as aggressive suction has the potential to lead to a hematoma and eventual tissue necrosis) to assist the cervix's natural elasticity to "undo" the process of dilation and effacement or to maintain a closed and thick cervix. It is also expected that this gentle suction could promote the building up of scar tissue in the cervix—a process that is sometimes witnessed in individuals that have had cervical procedures, such as cervical cancer removals (LEEP or cryotherapy)—that may lead to a cervix that maintains its constriction and elongation throughout forceful contractions that would otherwise promulgate dilation and effacement. The pressure gage 26 can be helpful in order to accurately assess the amount of tension placed on the cervix with the suction applied by the cervical cup 12 when the same is applied to the patient as shown in FIG. 2.

The cervical cup 12 can be made of polymeric materials, plastic, silicone, latex, rubber, metals, and other materials and could also vary in shape and size. Placement of the cervical cup 12 does not necessarily require the use of anesthesia, as it is less invasive than a cerclage. It could be placed with the help of a sterile speculum exam, followed by sterilely preparing the vaginal vault and drying of the vaginal vault with swabs.

Besides the use of the applied vacuum, as described, attachment of the cervical cup 12 to the cervix 36 may also be achieved using medical tape, suture, or cyanoacrylate glue or by a combination of these techniques. Cyanoacrylate glue has been shown to have antimicrobial properties, thus decreasing another cause of preterm birth—infection. This glue would also act as a type of cerclage, but with the added benefit of equilibric (uniform) traction placed on the cervix. One of the many drawbacks of a cerclage is the fact that there is not equilibric traction on the cervix and there is weakness at the point of the stitch. This can cause eventual "tearing through" of the cervix, whereas traction and glue may result in added tensile strength. Removal of such medical items after prolonged attachment to mucosa with cyanoacrylate glue has proven to be successful in other medical devices and areas of the body. In some embodiments the glue is applied to the inside of the cervical cup 12 at the time of fabrication. In other embodiments the glue is applied by the practitioner before placement of the cup.

Because of some evidence regarding chances that a break in the amnion may be prone to resealing and because the best outcomes for these patients is had in this resealing, some complex attempts have been made at finding a way to encourage this resealing, although this is not mainstream treatment. The proposed cervical cup may in fact encourage the resealing of the amnion due to its creation of a barrier at the external os of the cervix and has the ability to retain the amniotic fluid in situ.

Those of ordinary skill will appreciate that there are many types of vacuum generating sources or devices 24 that could be used with the applicator 20, including a bulb syringe type that generates a vacuum when the bulb is compressed. Any of these types of vacuum sources could be used to constrict and elongate the cervix, including electrically created vacuums or vacuums created by heating and/or cooling systems. Many other types of pressure gauges are also known and applicable to the subject matter disclosed besides the sliding ruler gauge 26 shown in FIG. 1. The type of pressure gauges and vacuum sources used do in no way limit the scope of the subject matter disclosed and claimed herein.

In one embodiment of the subject matter disclosed herein, the negative pressure applied to the cervix can be monitored by making the cup from a material that changes color depending on the pressure applied, especially at the base of the cup, thereby alerting a provider via sterile speculum exam to the increased risk of uterine contractions producing pressure great enough to create uterine rupture and thus expedite its removal. Another would be to have a pop-off valve (generally illustrated as element 28 in FIG. 1) somewhere on the cup that would release if the vacuum pressure exceeds a predetermined threshold value. If painful contractions continue to become more painful and frequent, the cervical cup may be removed in order to eliminate the chance of a uterine rupture. At 36 weeks of gestation, removal of the cup would be ideal regardless of the condition of the patient, as delivery of the fetus should happen thereafter.

Figure 3:
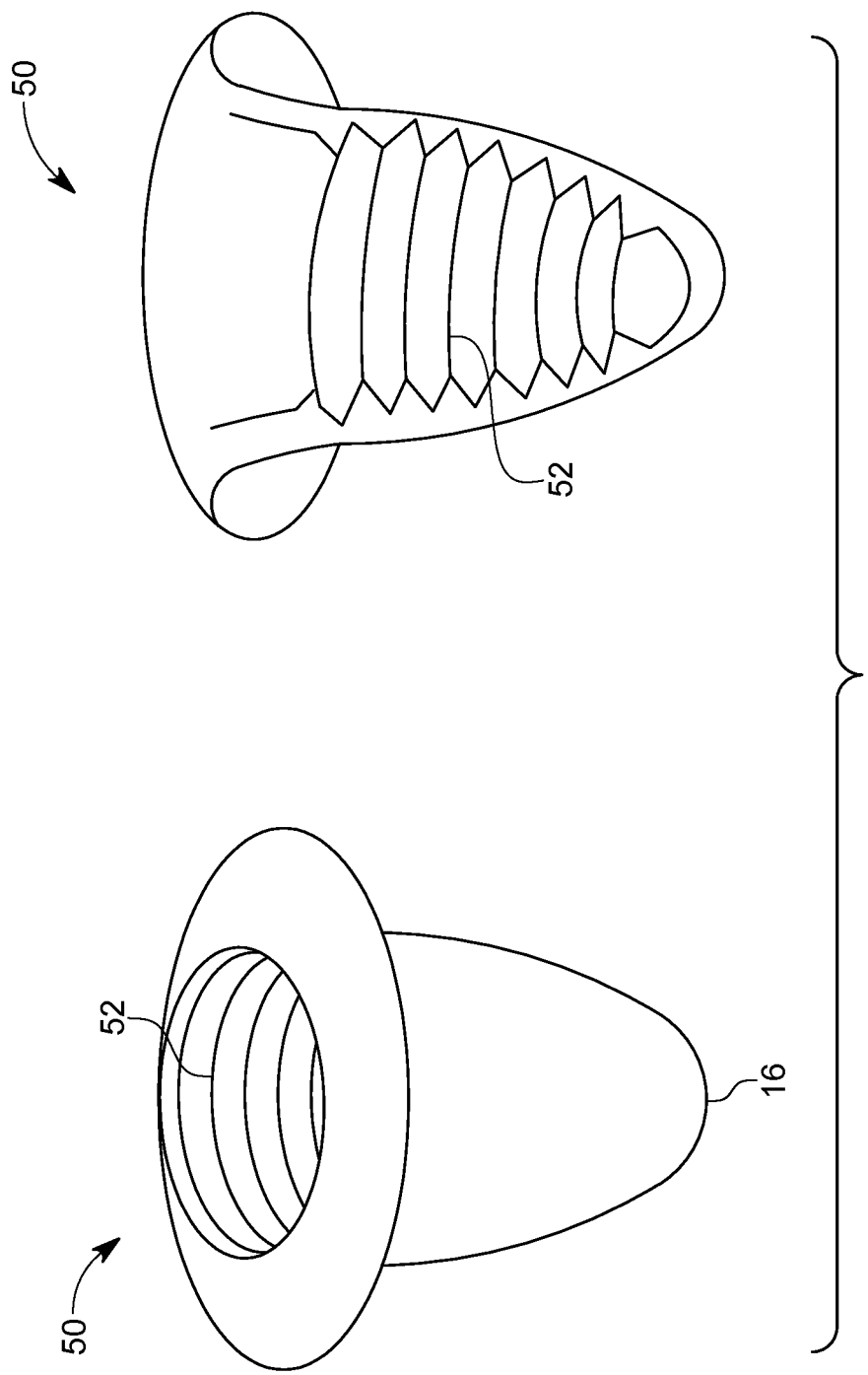
FIG. 3 illustrates perspective and sectional views of another exemplary embodiment of a threaded cervical cup according to another aspect of the subject matter disclosed.

There are many variations to the design of the cervical cup 12 that may help secure the goal of prolonging pregnancy. FIGS. 3-16 illustrate exemplary embodiments of some of these variations. FIG. 3 illustrates perspective and sectional views of another exemplary embodiment of a threaded cervical cup 50 according to another aspect of the subject matter disclosed. Placement of such cups could be implemented by use of threads 52 alone or by use of the applicator 20 connected to the connection port 16 and application of a gentle vacuum or any of the other placement techniques already explained. The cervical cup 50 with internal screw threads 52 will also be capable of mechanically constricting and elongating the cervix and drawing out the cervix as it is screwed into place. It may also help to maintain the cervix in place.

Figure 4:
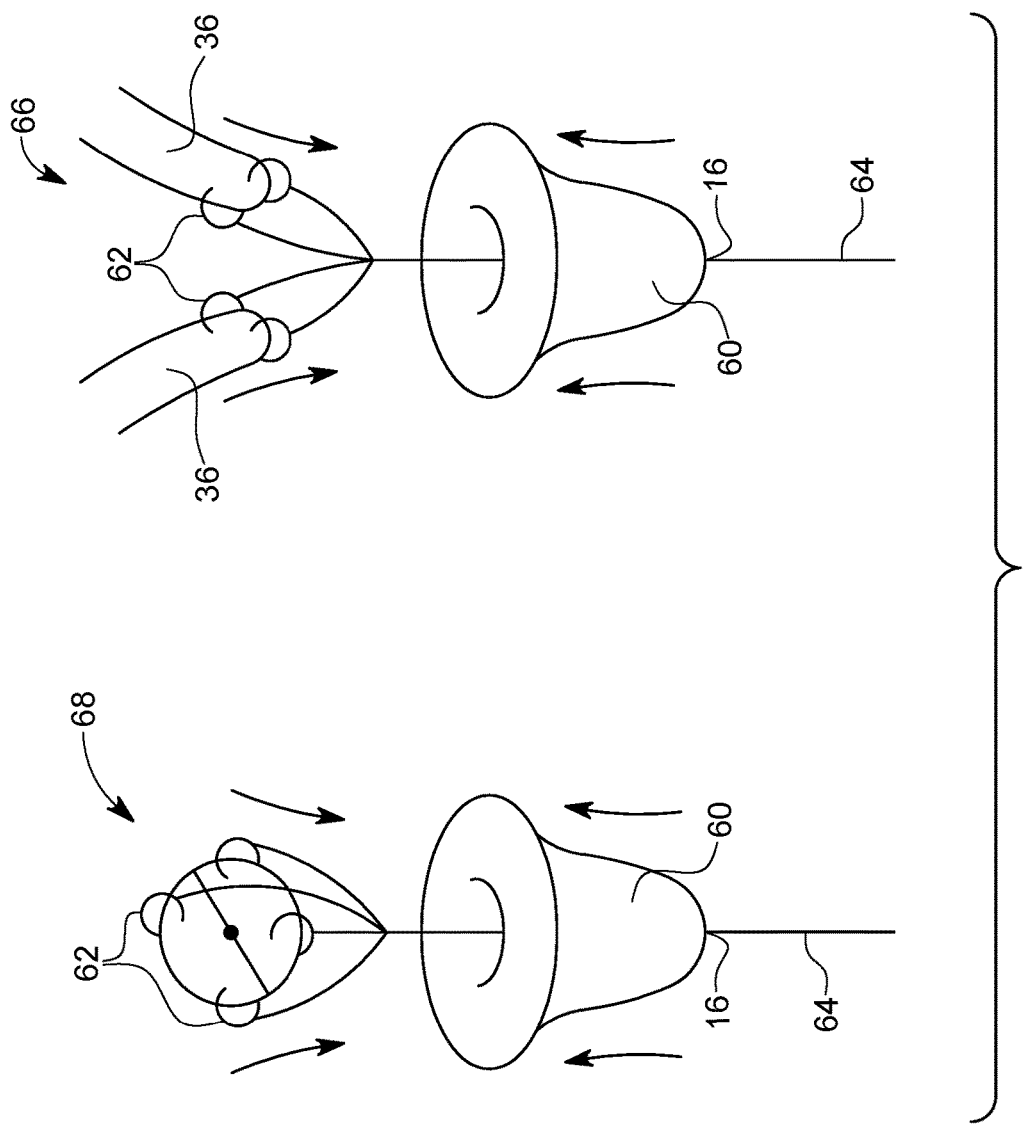
FIG. 4 illustrates another exemplary embodiment of a cervical cup that includes cervical clasps according to another aspect of the subject matter disclosed.

Another way to maintain, elongate, and constrict the cervix will be to retract the cervix using clasps or bands that attach themselves to the cervix, then using a pull string, wire or stylet to pull the cervix downward and place a cervical cup into place. FIG. 4 illustrates another exemplary embodiment of a cervical cup 60 that includes a single or a plurality of cervical clasps 62 connected to a guiding string, wire or stylet 64 according to another aspect of the subject matter disclosed. In the illustration on the right side of the figure at 66, the cervix clasps 62 are illustrated when the same are first placed on the cervix 36. The illustration on the left at 68 shows the view of an observer looking up at the cervix 36 from the position of the cup 60 before guiding the cervix 36 into the cup 60 by the guiding string, wire or stylet 64. Placement of such cups could be implemented by use of the guiding string, wire or stylet 64 alone or by use of the applicator 20 connected to the connection port 16 (through which the guiding string, wire or stylet 64 is also passed) and application of a gentle vacuum or any of the other placement techniques already explained. The cervical cup 60 with the cervical clasps 62 and guiding string, wire or stylet 64 will be useful to guide the cervices 36 into the cup 60 during placement without placing undue stress on the cervix 36.

Figure 5:
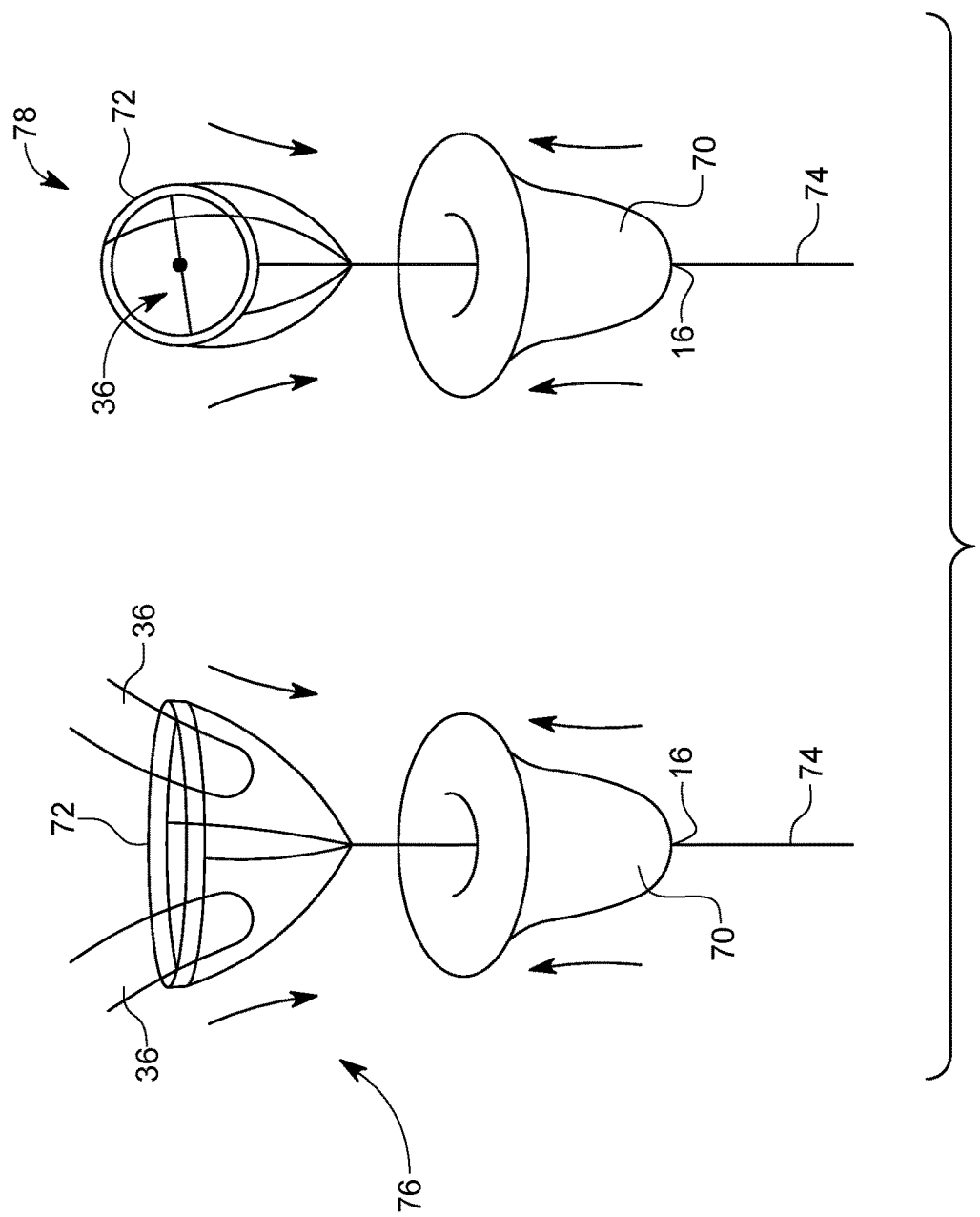
FIG. 5 illustrates another exemplary embodiment of a cervical cup that includes a cervical band according to another aspect of the subject matter disclosed.

FIG. 5 illustrates another exemplary embodiment of a cervical cup 70 that includes a cervical band 72 connected to a guiding string, wire or stylet 74 according to another aspect of the subject matter disclosed. In the illustration on the left side of the figure at 76, the cervical band 72 is illustrated when the same is first placed around the cervix 36. The illustration on the right at 78 shows the view of an observer looking up at the cervix 36 from the position of the cup 70 once the closed cervix 36 is ready to be gently brought into the cervical cup 70 by the guiding string, wire or stylet 74. Placement of such cups could be implemented by use of the guiding string, wire or stylet 74 alone or by use of the applicator 20 connected to the connection port 16 (through which the guiding string, wire or stylet 74 is also passed) and application of a gentle vacuum or any of the other placement techniques already explained. The cervical cup 70 with the cervical band 72 and guiding string, wire or stylet 74 will also be useful to guide the cervix 36 into the cervical cup 70 during placement without placing undue stress on the cervix 36.

Figure 6:
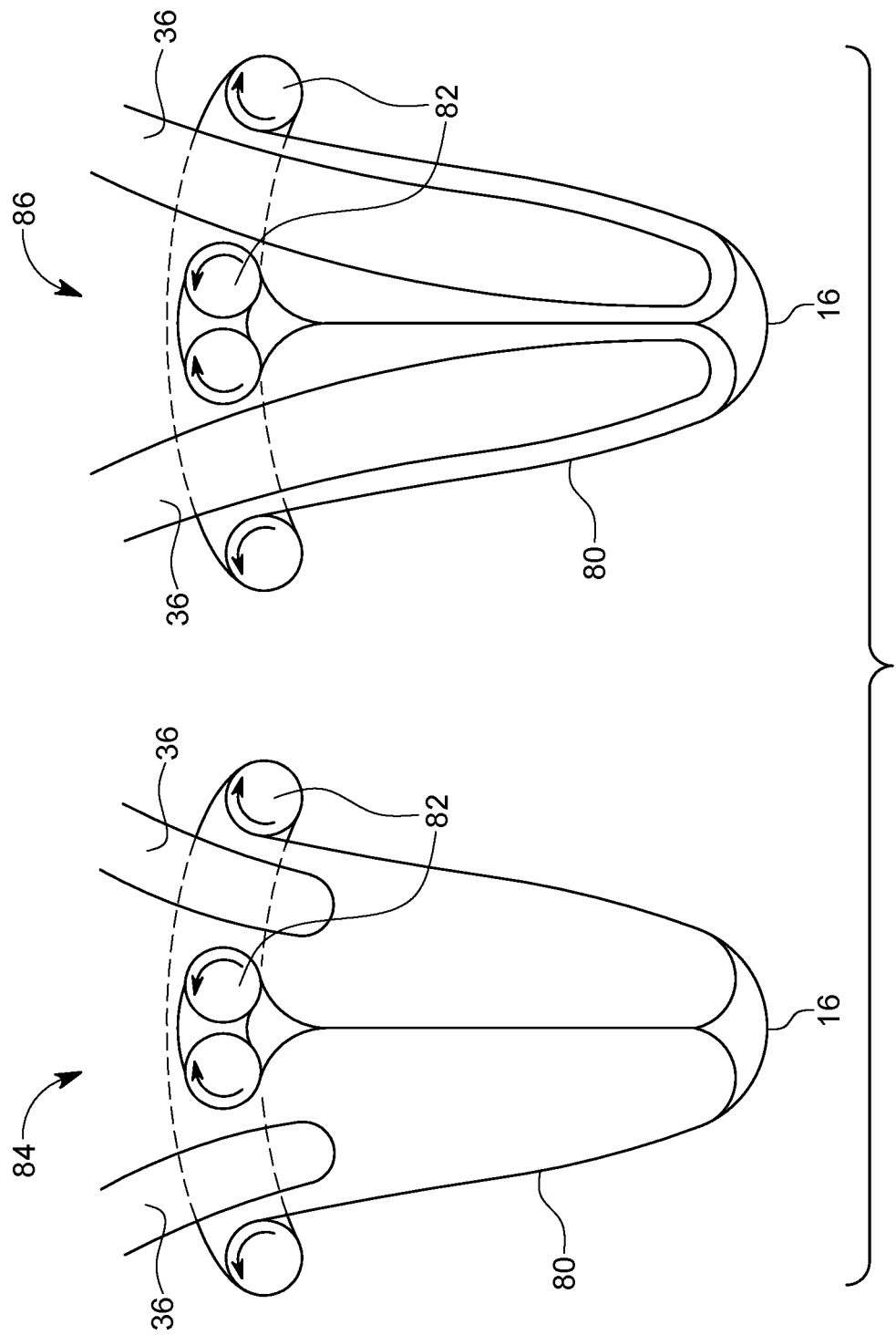
FIG. 6 illustrates a sectional view of another exemplary embodiment of a cervical cup that includes a gear system according to another aspect of the subject matter disclosed.

A gear system coupled to a cervical cup will be another way to maintain, elongate, and constrict the cervix. As the gears on the cup flange rotate outward and upward, the cervix moves downward into the cup. This movement will eventually create a meeting between the external os and the base of the cup and the internal os and the internal flange. FIG. 6 illustrates another exemplary embodiment of a cervical cup 80 that includes a gear system 82 according to another aspect of the subject matter disclosed. The illustration on the left side of the figure at 84 shows the cervix 36 when the same is first placed in contact with the gear system 82. The illustration on the right at 86 shows the cervices 36 fully disposed inside the cervical cup 80 once the cervix 36 is gently brought into the cervical cup 80 by the rolling action of the gear system 82. Placement of such cups could also be implemented by use of the applicator 20 connected to the connection port 16 and application of a gentle vacuum or any of the other placement techniques already explained once the cervix 36 is fully lodged inside the cervical cup 80.

Figure 7:
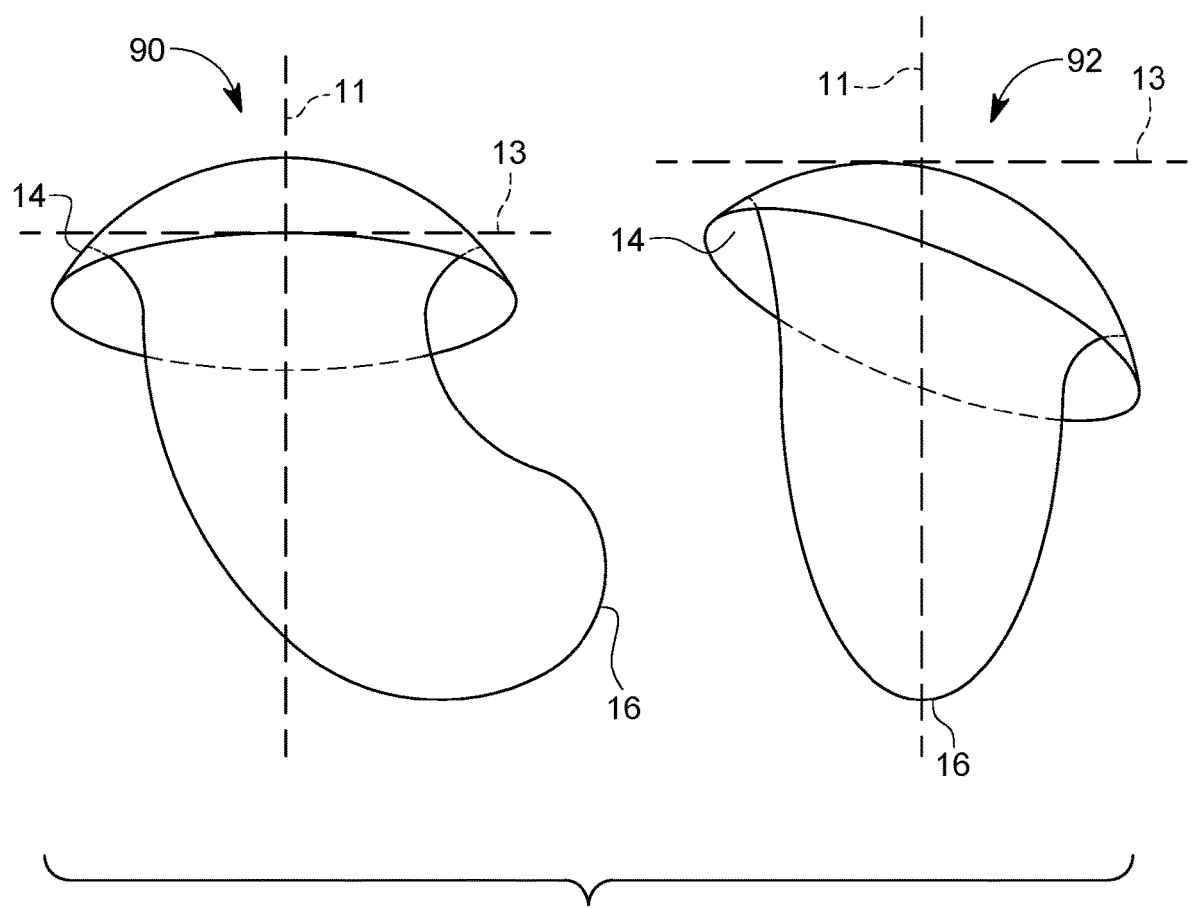
FIG. 7 illustrates other exemplary embodiments of a curved and tilted cervical cups according to other aspects of the subject matter disclosed.

FIG. 7 illustrates other exemplary embodiments of a curved 90 and tilted 92 cervical cups according to another aspect of the subject matter disclosed. Those of ordinary skill in the art will appreciate that the capability of controlling the position of the cervix inside the vagina may affect the duration of gestation because women having the cervix in a posterior position (pointing to the back) are known to be further from the time of parturition than women with cervices in other positions. So, cervical cups shaped so as to allow the cervix to be pointed in a preferred direction would benefit from such embodiments. This may be accomplished by the curved cervical cup 90 on the left side of FIG. 7 or by the tilted cervical cup 92 on the right side of FIG. 7. As illustrated, a curved cervical cup has its main body curved with respect to its radial axis perpendicular to the page (not label in the figure) so as to create asymmetry about the axial axis 11 while the tilted cup has its main body generally aligned with the axial axis 11 with the flange 14 tilted with respect to the radial axis 13. Placement of the cervical cups 90 and 92 could also be implemented by use of the applicator 20 connected to the connection port 16 and application of a gentle vacuum or any of the other placement techniques already explained once the cervix 36 is fully lodged inside the cervical cups 90 or 92.

Figure 8:
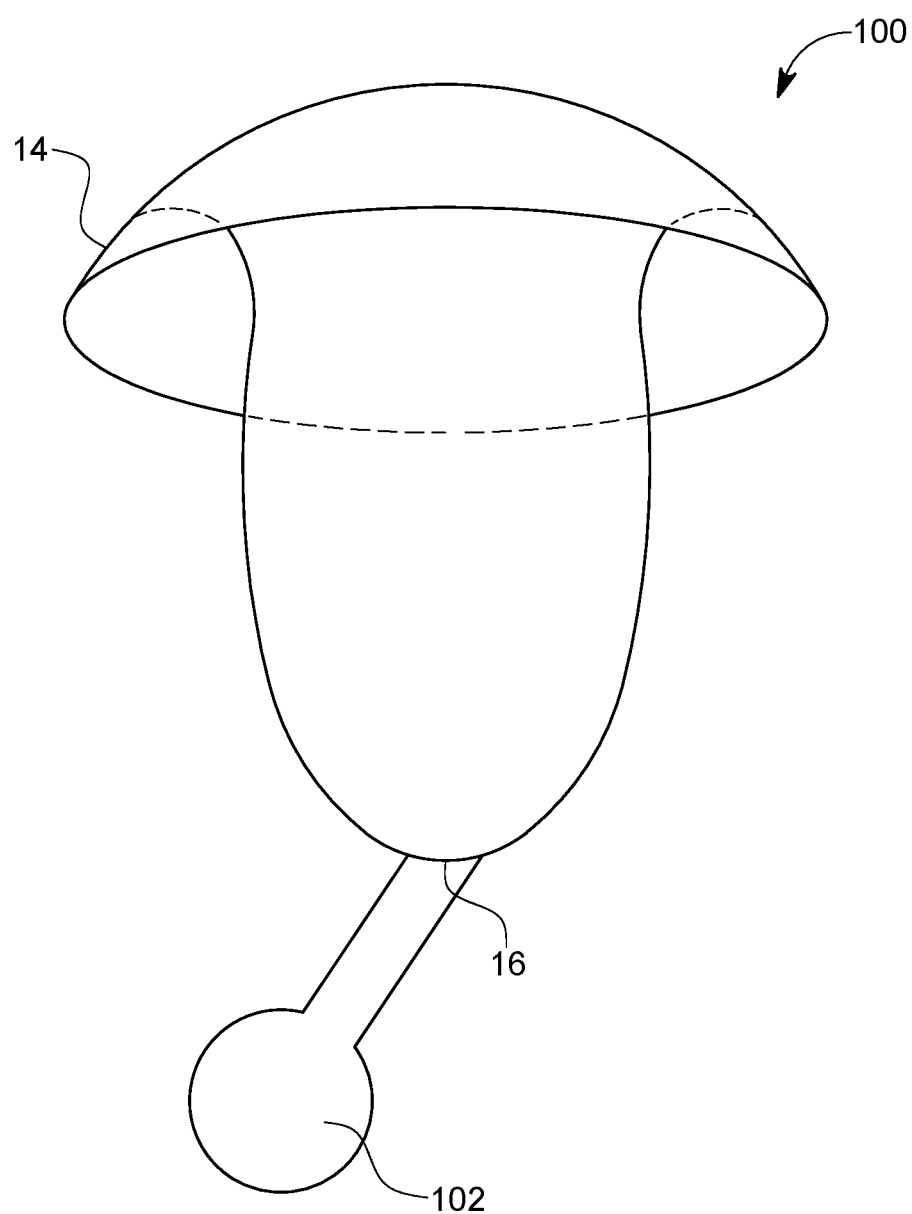
FIG. 8 illustrates another exemplary embodiment of a cervical cup that includes a positional stand according to another aspect of the subject matter disclosed.

FIG. 8 illustrates another exemplary embodiment of a cervical cup 100 that includes a positional stand 102 according to another aspect of the subject matter disclosed. Those of ordinary skill in the art will appreciate that the positional stand 102 will augment the capability of controlling the position of the cervix inside the vagina 38 during the placement of the cervical cup 100 but also during extended periods of time by serving as a support to keep the cervical cup 100 in the desired position. Placement of the cervical cup 100 could also be implemented by use of the applicator 20 connected to the connection port 16 and application of a gentle vacuum or any of the other placement techniques already explained once the cervix 36 is fully lodged inside the cervical cup 100.

Figure 9:
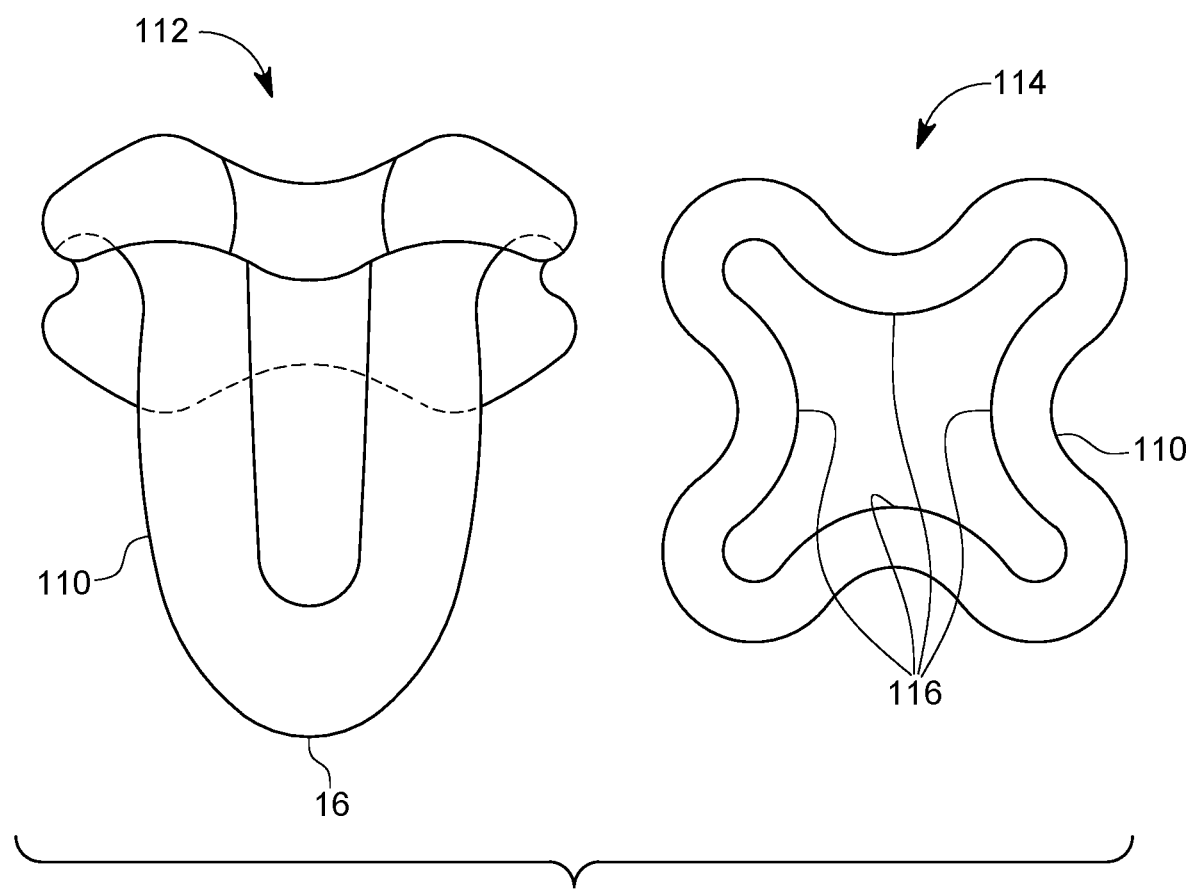
FIG. 9 illustrates perspective and top views of another exemplary embodiment of a corrugated cervical cup according to another aspect of the subject matter disclosed.

FIG. 9 illustrates perspective (at 112) and top (at 114) views of another exemplary embodiment of a corrugated cervical cup 110 according to another aspect of the subject matter disclosed. Those of ordinary skill in the art will appreciate that the corrugations 116 may provide an added element of stability following placement of the corrugated cervical cup 110. Placement of the corrugated cervical cup 110 could also be implemented by use of the applicator 20 connected to the connection port 16 and application of a gentle vacuum or any of the other placement techniques already explained once the cervix 36 is fully lodged inside the corrugated cervical cup 110.

Figure 10:
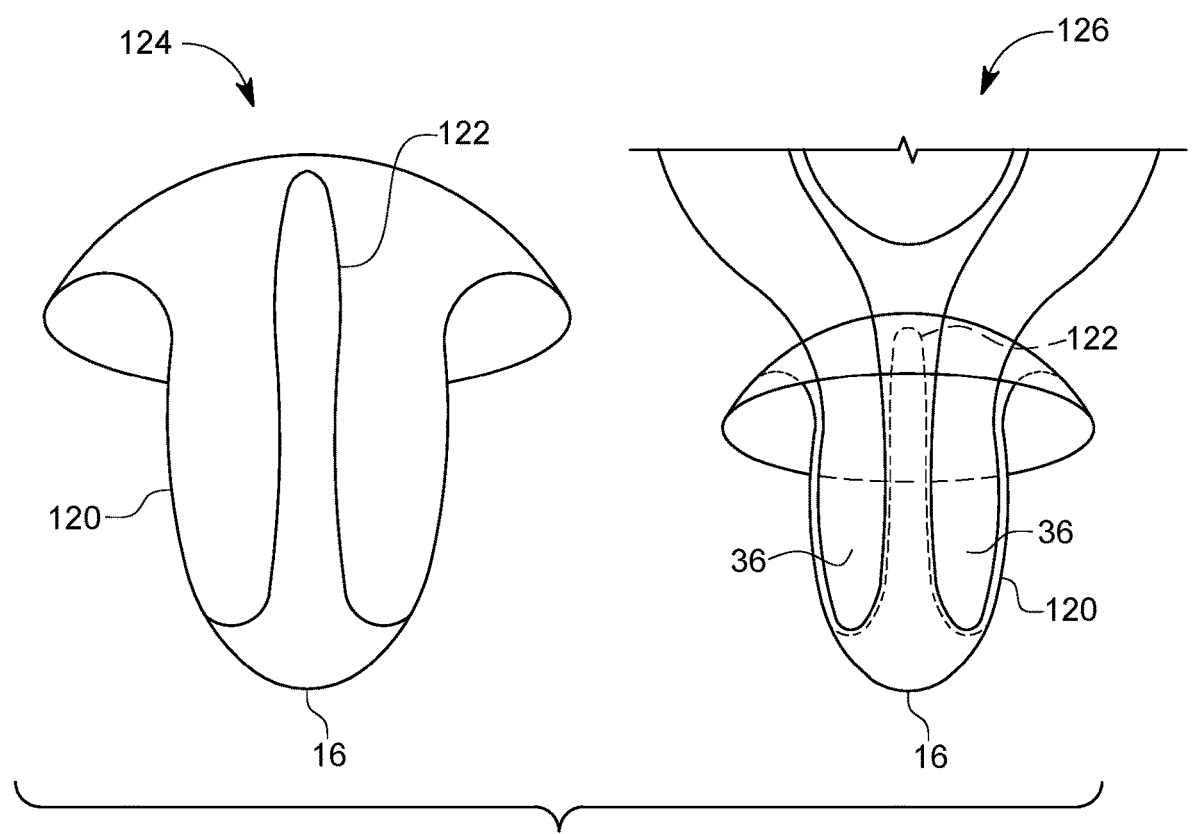
FIG. 10 illustrates another exemplary embodiment of a cervical cup that includes a post and placement of this cervical cup on a pregnant woman according to another aspect of the subject matter disclosed.

FIG. 10 illustrates another exemplary embodiment of a cervical cup 120 that includes a post 122 according to another aspect of the subject matter disclosed. The illustration on the left side of the figure at 124 shows the cervical cup 120 with the post 122. The illustration on the right at 126 shows the cervix 36 fully disposed inside the cup 120 with the post 122 inserted into the cervical canal, substantially and effectively lining and occluding the cervical canal. This post 122 can also assist in lining and occluding the cervical canal when the internal os is closed but the external os is open, a presentation seen in some cases of cervical insufficiency, PPROM, and preterm labor. Placement of such cups could also be implemented by use of the applicator 20 connected to the connection port 16 and application of a gentle vacuum or any of the other placement techniques already explained once the cervix 36 is fully lodged inside the cervical cup 120. One of the advantageous features of the post 122 is that it can help occlude the cervical canal from undesirable exposure and mitigating the risk of infection, thus prolonging the pregnancy term. Sometimes the cervix of a dilated woman will not close completely so the post 122 would help to keep the cervix closed. Post of different lengths and/or diameters could be used to fill the cervical canal depending on the amount of dilation.

Figure 11:
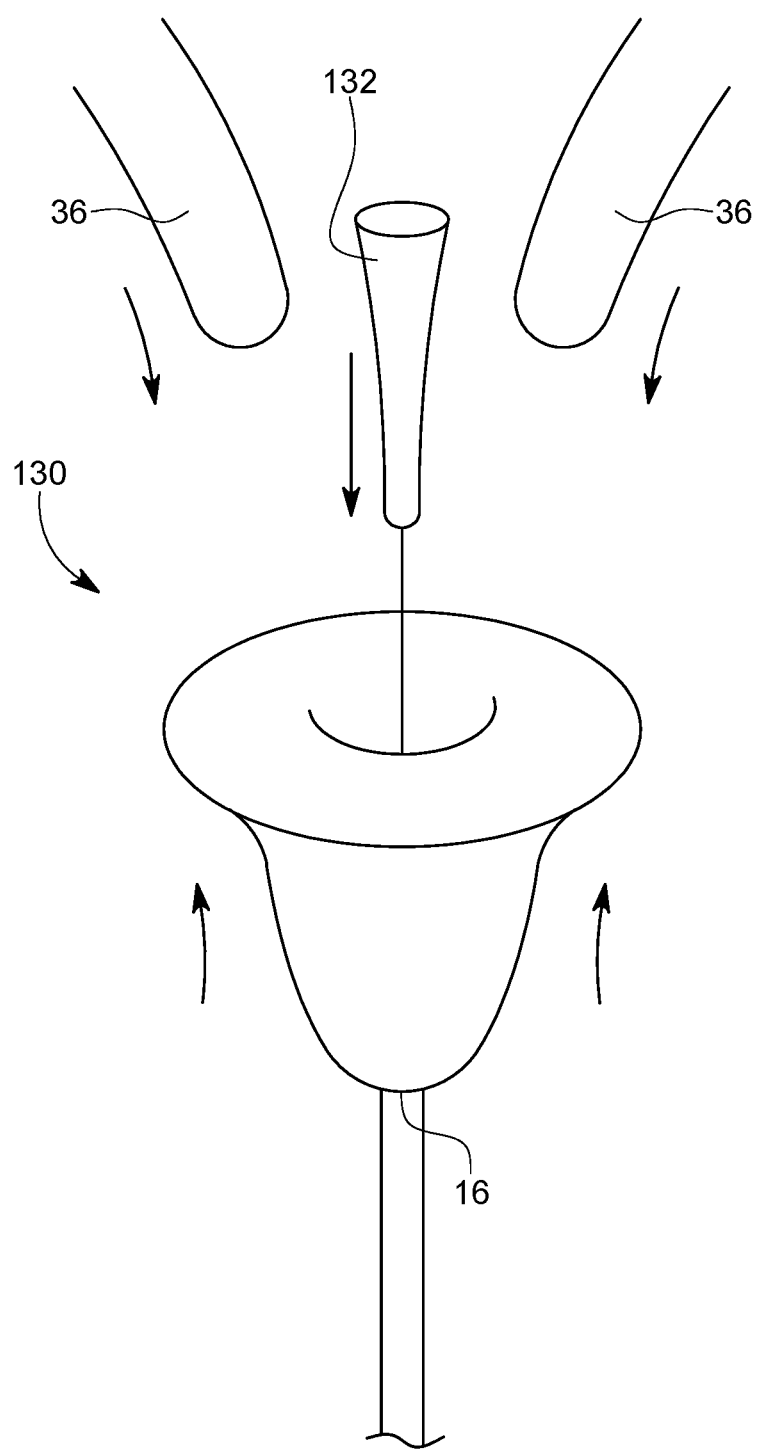
FIG. 11 illustrates another exemplary embodiment of a retractable double cervical cup according to another aspect of the subject matter disclosed.
Figure 12:
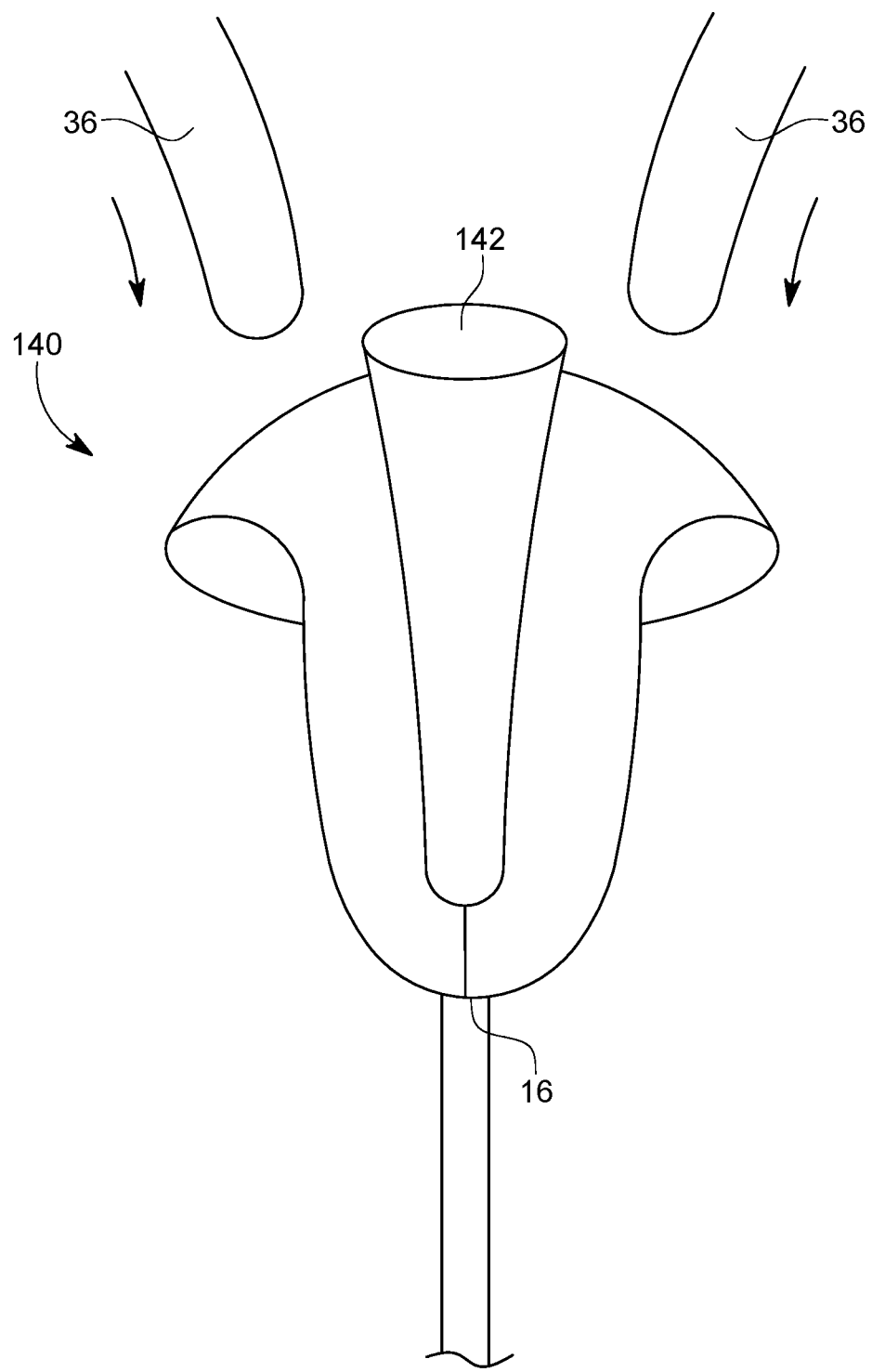
FIG. 12 illustrates another exemplary embodiment of a stationary double cervical cup according to another aspect of the subject matter disclosed.

FIGS. 11 and 12 illustrate other exemplary embodiments of a retractable double cervical cup 130 and a stationary double cervical cup 140, respectively, according to other aspects of the subject matter disclosed. FIG. 11 illustrates the inner cup raised for placement while FIG. 12 illustrates the inner cup following placement or as a stationary cup. These inner cups could be either stationary or retractable and will also aide in directing the cervix to enter the cup with more precision, as well as filling the internal cervical os. This could help with stabilizing the cervix and keeping the cup in place. Again, differing sized inner cups could fill the internal cervical os depending on the amount of dilation. Both secondary portions or posts 132 and 142 can also serve as an occlusion for the internal cervical os, thereby preventing undesirable exposure and mitigating the risk of infection. Placement of such cups could also be implemented by use of the applicator 20 connected to the connection port 16 and application of a gentle vacuum or any of the other placement techniques already explained once the cervix 36 is fully lodged inside the illustrated cups 130 and 140.

Figure 13:
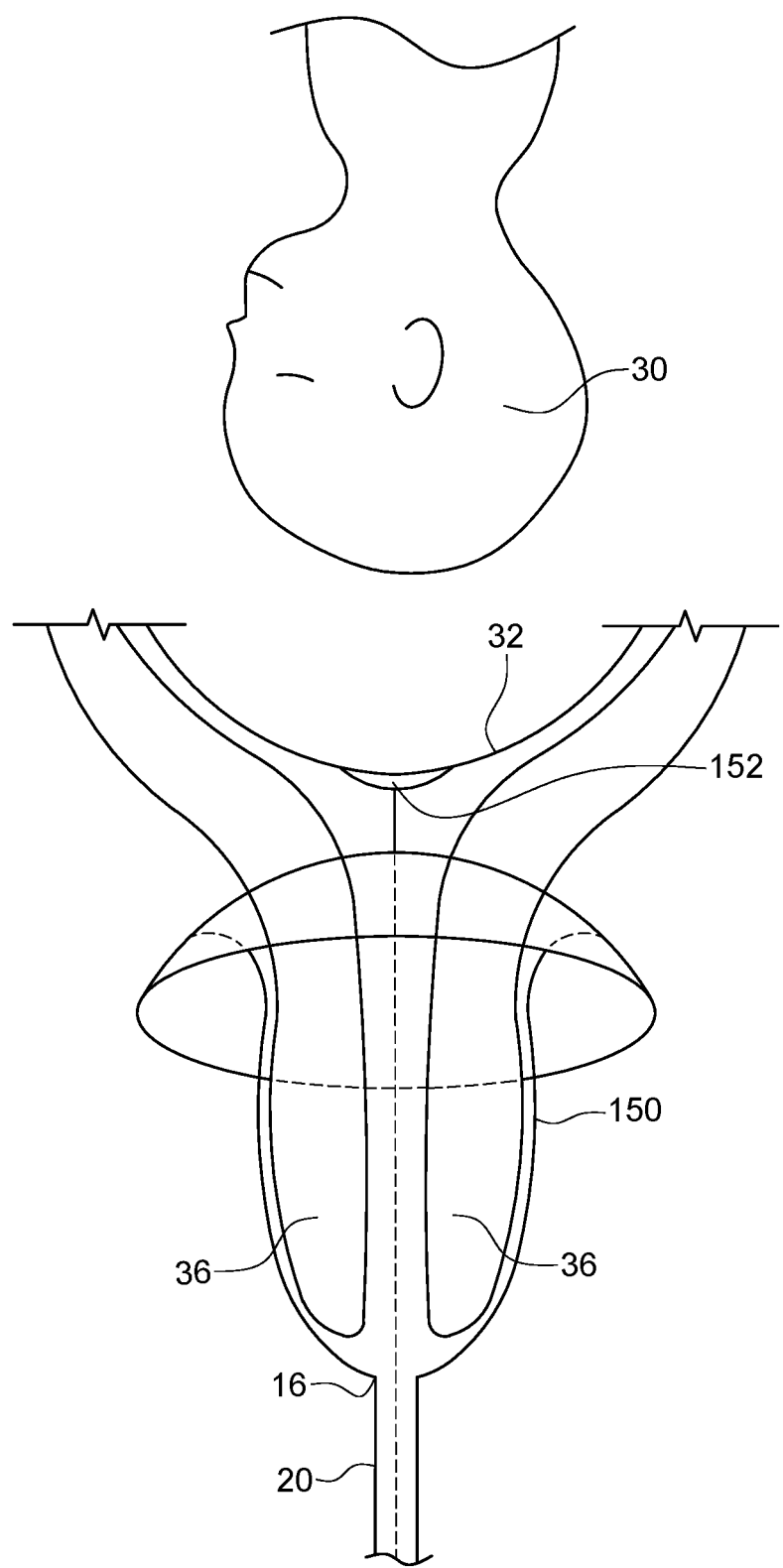
FIG. 13 illustrates another exemplary embodiment of a cervical cup that includes an amnion shield and placement of this cervical cup on a pregnant woman according to another aspect of the subject matter disclosed.

FIG. 13 illustrates another exemplary embodiment of a cervical cup 150 that includes an amnion shield 152 according to another aspect of the subject matter disclosed. One population that needs special consideration is that of women diagnosed with telescoping membranes, or membranes that have come through the cervical os. This is a phenomenon that is difficult to treat, as any stimulation of the cervix or amnion could cause the amnion to rupture, but the dilating cervix and the telescoping amnion need to be addressed. Some practitioners feel the best course of action is to attempt a rescue cerclage while others feel expectant management is best, relying on things like patient position to control the downward pull of gravity on the amnion. The cervical cup 150 with the amnion shield 152 may be a better course of treatment for these women. The separation of the shield 152 from the cervical cup 150 can be made adjustable depending on the amount of telescoping displacement of the amnion 32. The shield could gently reintroduce the amnion back into the uterine cavity and then could protect the amnion from the pull of the device, while still allowing for closure of the cervix. This, of course, could raise the likelihood of rupture of the amnion, but the benefit may outweigh the risk and, as stated earlier, if rupture does happen, the cup may also be of use. Placement of a telescoping amnion in a desired position has been proven in the past to be effective in removing the amnion from the cervical os, allowing for a cervical cerclage to be placed, and has resulted in extending the pregnancy.

Figure 14:
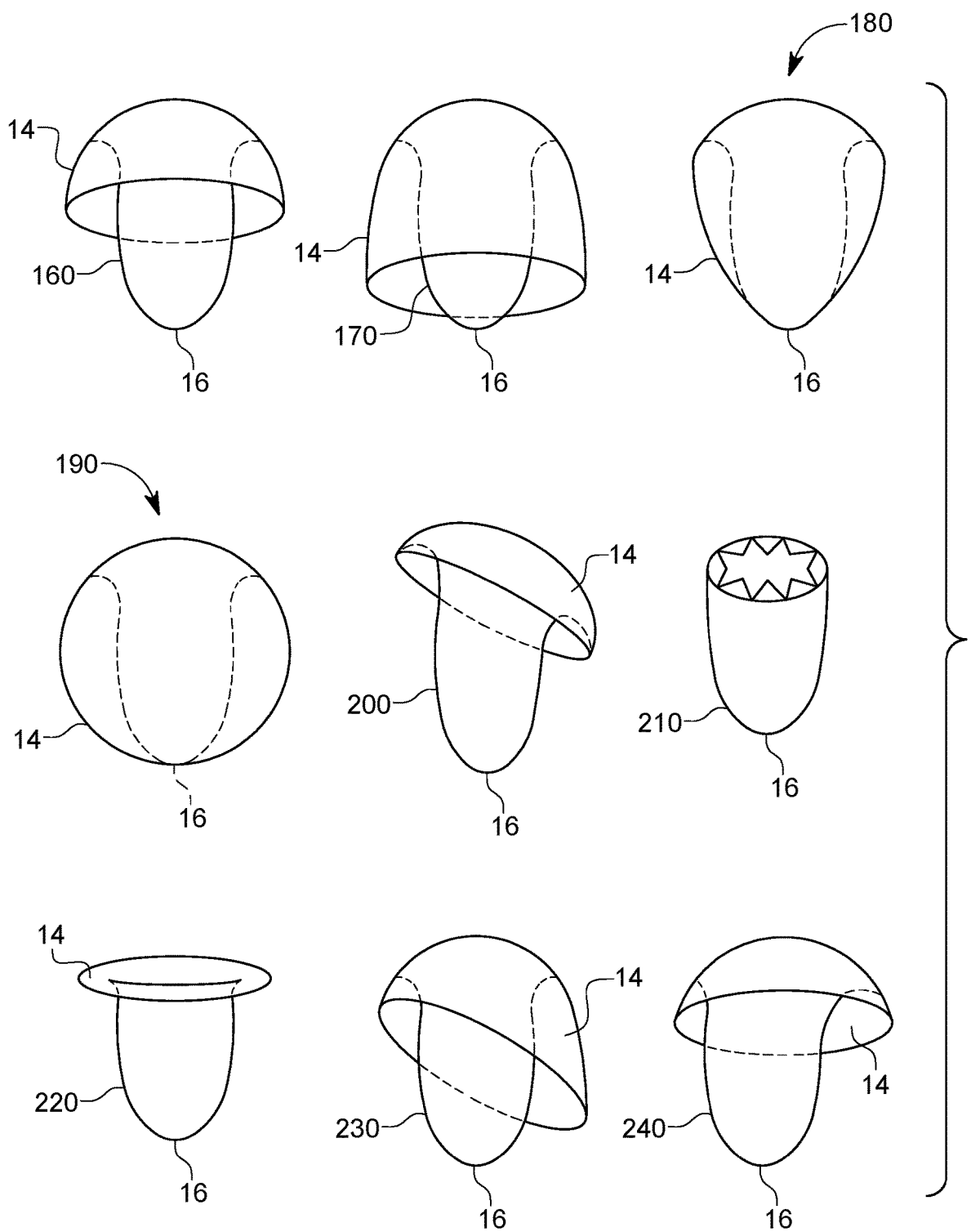
FIG. 14 illustrates various other exemplary embodiments of varying shapes of flanges and bodies for cervical cups according to various other aspects of the subject matter disclosed.

FIG. 14 illustrates various other exemplary embodiments of varying shapes of flanges and bodies for cervical cups (160-240) according to various other aspects of the subject matter disclosed. As shown and previously explained, at the lip of the cup, a flange could be an option which would help displace the downward pressure that is created by the presenting part applying itself to the cervix—one of the mechanical reasons for cervical change. These flanges would also enable the mother to feel less suprapubic pressure from the resulting "lift." These flanges could also be placed in such a way as to tip the cervix posteriorly, adding to the effect of continued quiescence. The flange depicted in 160 is a flange of medium length that would provide a medium amount of "lift" to displace the downward pressure created by the presenting part. The flange depicted in 170 is a long flange that would provide a larger amount of "lift" to displace the downward pressure created by the presenting part, possibly making this flange ideal for mothers of multiple gestation. The flange depicted in 180 is a flange that progresses inward toward the apex of the cup 16 adding to the comfort for the woman as it sits in the vagina 38. The flange depicted in 190 has a flange that the edges curve outward resulting in a greater "lift" while curving towards the apex of the cup 16 in a convex pattern continuing to add to the comfort for the woman as it sits in the vagina 38. The cervical cup 200 (similar to the cervical cup 92 in FIG. 7) will aide in positioning the cervix in the posterior position. The flange depicted in 210 without a flange and with alternating gripping grooves and protrusions inside of the body of the cup may grip the cervix and hold the cup in place. The flange depicted in 220 is a flange of no length extending downward toward the apex of the cup that may help women where there is not a significant amount of downward pressure created by the presenting part, such as in women where the fetus presents as breech. The flange depicted in 230 having a flange that extends toward the apex of the cup on a slanted fashion with respect to the radial axis of the cup may help change the uterocervical angle towards the posterior position as there will be less "lift" on the short edge of the flange and more "lift" on the longer edge. The flange depicted in 240 sits on the cup 16 in an asymmetrical pattern that would add more "lift" at the greater portion on the flange and less "lift" at the lesser portion of the flange, resulting in a posterior position of the cup 16 and cervix 36.

Figure 15:
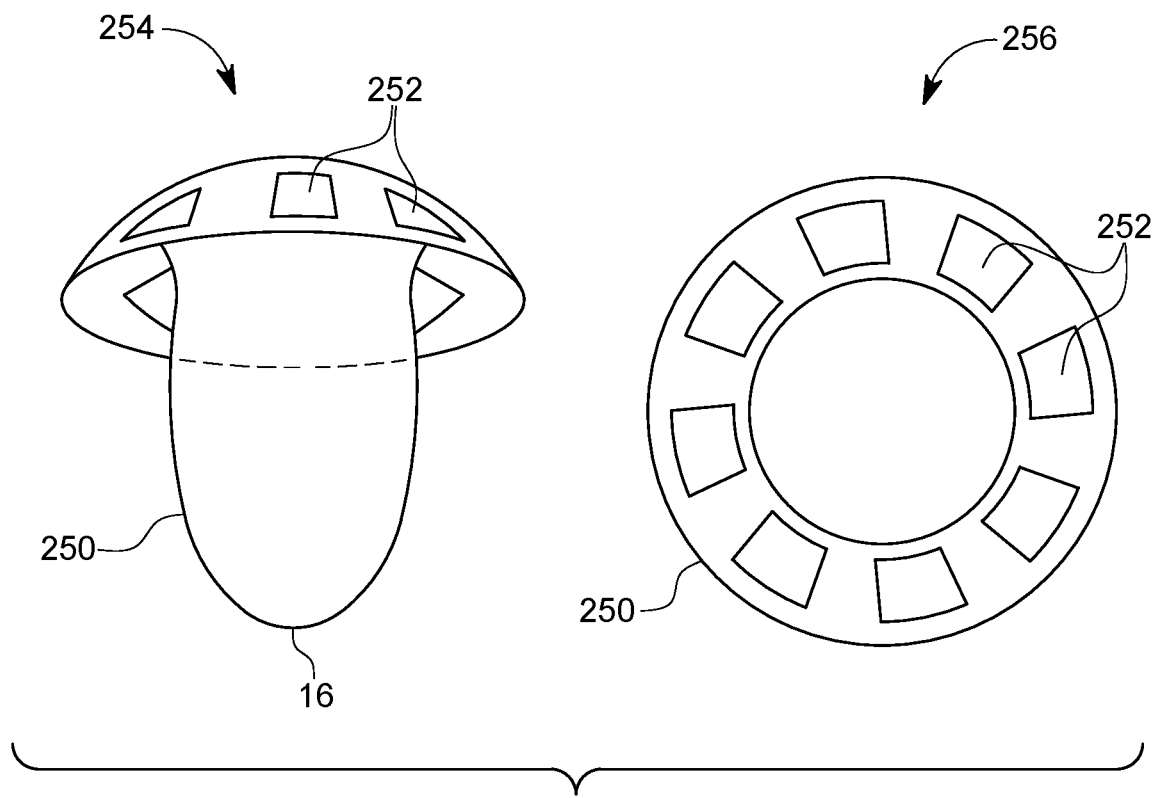
FIG. 15 illustrates perspective and top views of another exemplary embodiment of a vented cervical cup according to another aspect of the subject matter disclosed.
Figure 16:
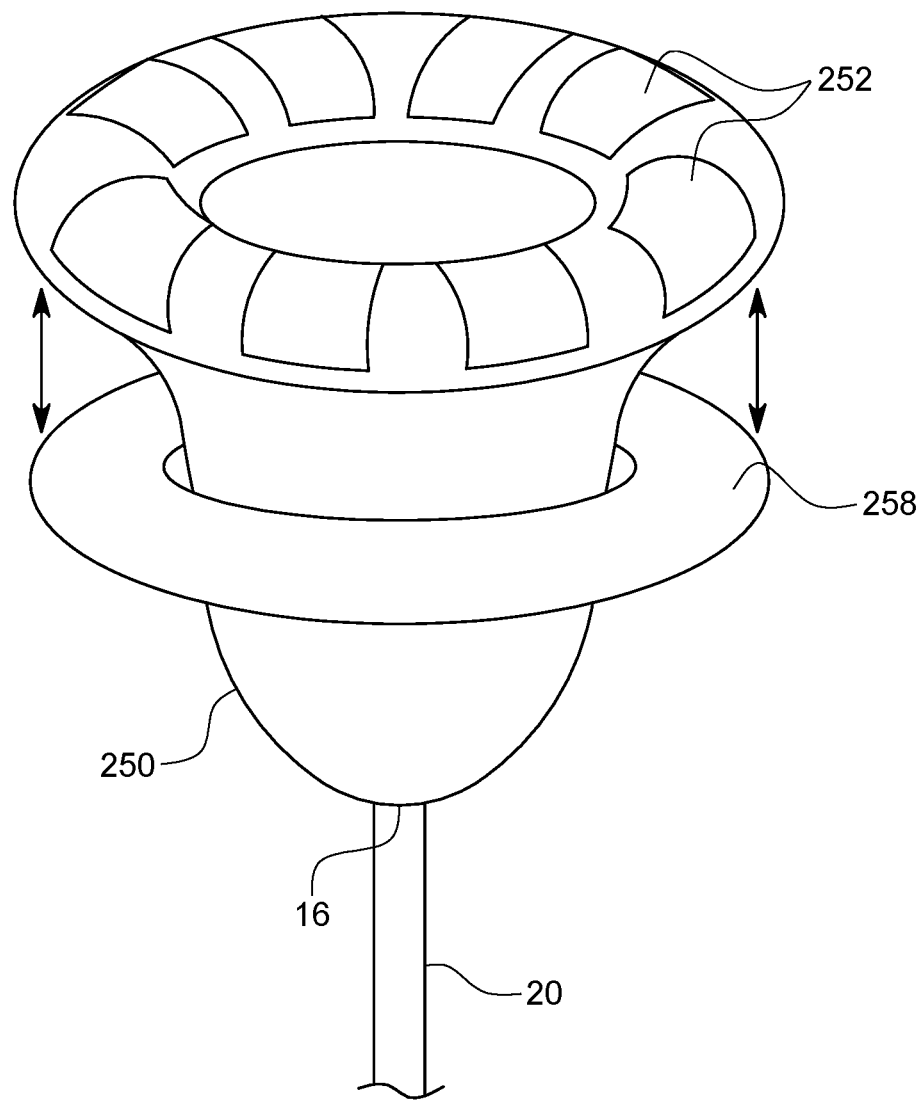
FIG. 16 illustrates the application of a medicated ring to the cervical cup of FIG. 15.

FIG. 15 illustrates perspective (at 254) and top (at 256) views of another exemplary embodiment of a vented cervical cup 250 according to another aspect of the subject matter disclosed. FIG. 16 illustrates the application of a medicated ring 258 to the vented cervical cup 250 of FIG. 15. Those of ordinary skill will appreciate that a flange with vents 252 can be an option that may be of benefit if the vented cervical cup 250 is attached with suture and also may help in cervical mucous drainage.

In order to better provide care for mothers experiencing the possibility of preterm delivery, practitioners should address both the chemical and mechanical reasons for labor. To better address both of these aspects of care, the vented cervical cup 250 could have the added benefit of disseminating medication if a practitioner so desired. Any number of medications could be administered this way, including, but not limited to, antibiotics, tocolytics, steroids or hormones, and/or medications discovered in the future. Both a medicated and an unmedicated version of the vented cervical cup 250 could be of use if providers wish to manage the pharmacologic concerns of their patient through other means. Although any piece of the cup may be used to administer medication (i.e., the vents 252 don't necessarily have to be disposed on the flange of the cup as shown in FIGS. 15 and 16), the flange may be one advantageous place. Another option may be to have a removable medication releasing polymeric vaginal ring. Further, none of these options would be a contraindication for antibiotics, tocolytics, steroids or hormones and the cup may enhance their efficacy.

As already explained, any combination of these ideas may prove to be successful at mitigating the damages of preterm birth. Such cervical cups would greatly benefit the toolbox of obstetric providers worldwide, as there are two things that aide such providers: helping infants stay in utero and helping infants exit the uterus. There are no conventional devices and/or procedures that perform the former and fewer still that address both the chemical impetus and the mechanics of labor.

Those of ordinary skill will appreciate that the cervical cups disclosed herein will be an effective treatment for PPROM because it would seal off the amniotic sac (amnion) and could have the fluid replenished if indicated due to oligohydramnios or anhydramnios. It would also potentially decrease the risk of infection so the pregnancy could be sustained longer. It too would be able to decrease the amount of effective contractions and to therefore decrease the likelihood of PPROM leading to preterm labor and delivery. Because of some evidence regarding chances that the break in the amnion may be prone to resealing and because the best outcomes for these patients is had in this resealing, some complex attempts have been made at finding a way to encourage this resealing, although this is not mainstream treatment.

There have been some studies surrounding the benefits of "resealing" the amnion after PPROM. These studies mainly looked at the effects of highly invasive procedures, but the disclosed cervical cups will be a less invasive viable option. It would potentially enable the amnion to seal itself. Even in the event of resealing not taking place, it still would possibly aide in the raising of the amniotic fluid index—or the amount of amniotic fluid in the uterine cavity—since the amniotic fluid would not be draining out of the cervix after the cervical cup is placed and maintained. It would also be possible to allow practitioners to replace missing fluid with normal saline through amniocentesis/amnioinfusion.

It is expected that the cervical cups disclosed herein will prolong pregnancy in the face of preterm labor as well. At what point removal should happen is unknown and further research and testing will be required. It may be safest not to place the cervical cup disclosed herein on a woman in preterm labor with history of a previous uterine surgery or a classical uterine incision, as this could potentially increase her chances of uterine rupture. But many mothers presenting with contractions and slight cervical change could benefit from tocolytics and the cup without major complications.

Figure 17:
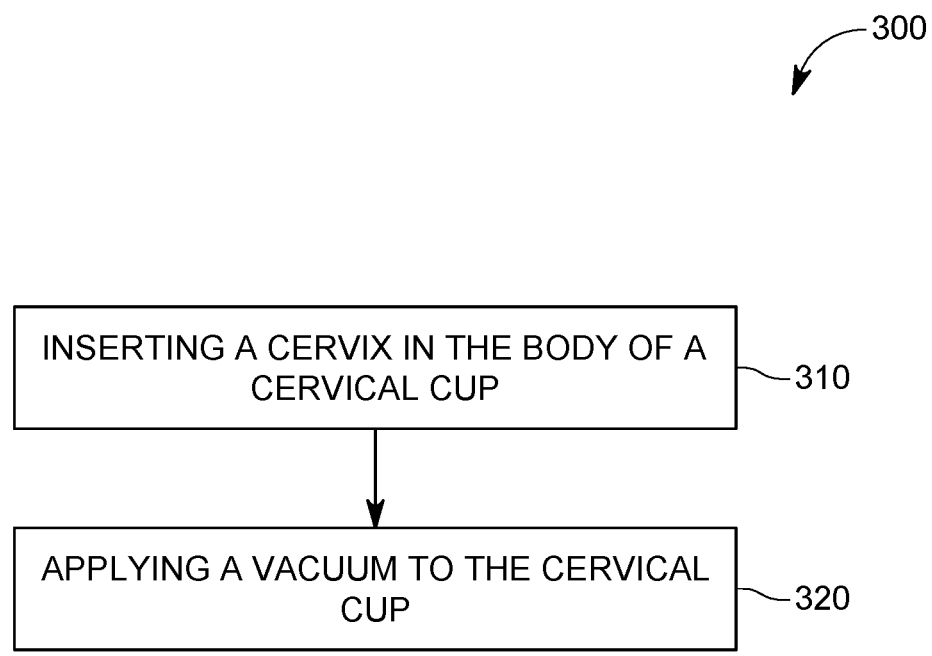
FIG. 17 illustrates a flowchart of a method to treat preterm births according to an embodiment of the subject matter disclosed.

Methods and processes to treat preterm births are also within the scope of the subject matter disclosed. FIG. 17 illustrates the flowchart of an exemplary embodiment of a method or process 300 according to the subject matter disclosed. As shown, at 310, such methods includes inserting end portions of a cervix into a cervical cup, the cervical cup having a body generally extending along an axial axis thereof, a flange attached to a proximal end portion of the body, and a vacuum port disposed at a distal end portion of the body; and, at 320, applying a vacuum to the vacuum port so as to secure the cervical cup to the cervix disposed inside of the body.

The disclosed exemplary embodiments provide apparatuses, methods, and systems for the treatment of preterm births and it should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments might be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

While the disclosed embodiments of the subject matter described herein have been shown in the drawings and fully described above with particularity and detail in connection with several exemplary embodiments, it will be apparent to those of ordinary skill in the art that many modifications, changes, and omissions are possible without materially departing from the novel teachings, the principles and concepts set forth herein, and advantages of the subject matter recited in the appended claims. Hence, the proper scope of the disclosed innovations should be determined only by the broadest interpretation of the appended claims so as to encompass all such modifications, changes, and omissions. In addition, the order or sequence of any process or method steps may be varied or re-sequenced according to alternative embodiments. Finally, in the claims, any means-plus-function clause is intended to cover the structures described herein as performing the recited function and not only structural equivalents, but also equivalent structures.

What is claimed is:

1. A cervical cup, comprising:
   a body generally extending along a first direction along an axial axis thereof, said body being generally curved and open at a proximal end;
   a flange attached to the proximal end of said body;
   a vacuum port connected to the body at a distal end of said body, and
   a valve connected to the vacuum port, said valve being configured to maintain a vacuum when a vacuum source is disconnected from the cervical cup,
   wherein, said body is curved with respect to a radial axis thereof so as to create asymmetry about the axial axis and the cervical cup is adapted to secure a cervix disposed inside of the body with an application of the vacuum to said vacuum port.

2. The cervical cup according to claim 1, wherein the flange is tilted with respect to the axial axis of the body.

3. The cervical cup according to claim 1, wherein the flange is an integral part of the body and formed by a curvature of the proximal end of the body to form a lip and the proximal end of the body extends past the lip in a second direction generally opposite to the first direction such that the curved end portion forming the flange radially extends away from the body.

4. The cervical cup according to claim 3, wherein an amount of lift to displace a downward pressure created by a presenting part of a fetus is determined by a length of the lip of the cervical cup.

5. A cervical c comprising:
   a body extending generally along a first direction along an axial axis thereof, said body being generally curved and open at a proximal end;
   a flange attached to the proximal end of said body;
   a vacuum port connected to the body at a distal end of said body,
   wherein, said body is curved with respect to a radial axis thereof so at to create asymmetry about the axial axis and the cervical cup is adapted to secure a cervix disposed inside of the body with an application of a vacuum to said vacuum port, the cervical cup further comprising:
   a layer of glue disposed on an inner surface of the body to assist in securing the cervix to the cervical cup.

6. The cervical cup according to claim 1, further comprising:
   a plurality of vents disposed on the flange.

7. The cervical cup according to claim 6, further comprising:
   a medicated ring disposed around an external surface of the body adjacent to the flange, said medicated ring being configured to administer a medication to the cervix through the plurality of vents.

8. A cervical cup, comprising:
   a body generally extending along a first direction along an axial axis thereof, said body being generally curved and open at a proximal end portion thereof;
   a flange formed by a curvature of the proximal end of the body to form a lip and the proximal end of the body extends past the lip in a second direction generally opposite to the first direction such that the curved end portion forming the flange radially extends away from the body;
   a vacuum port connected to the body at a distal end portion of said body; and
   a valve connected to the vacuum port, said valve being configured to maintain a vacuum when a vacuum source is disconnected from the cervical cup,
   wherein, the cervical cup is adapted to secure a cervix disposed inside of the body with an application of the vacuum to said vacuum port.

9. The cervical cup according to claim 8, wherein the flange is tilted with respect to the axial axis of the body.

10. The cervical cup according to claim 8, wherein said body is curved with respect to a radial axis thereof so as to create asymmetry about the axial axis.

11. The cervical cup according to claim 8, wherein said flange is an integral part of the body.

12. The cervical cup according to claim 8, further comprising:
    a plurality of vents disposed on the flange; and
    a medicated ring disposed around an external surface of the body adjacent to the flange, said medicated ring being configured to administer a medication to the cervix through the plurality of vents.

13. The cervical cup according to claim 8, wherein an amount of lift to displace a downward pressure created by a presenting part of a fetus is determined by a length of the lip of the cervical cup.

14. A method to treat preterm birth, the method comprising:
  inserting end portions of a cervix into a cervical cup, said cervical cup comprising a body generally extending along an axial axis thereof, a flange attached to a proximal end portion of said body, and a vacuum port disposed at a distal end portion of said body;
  inducing tension to the cervix by applying a vacuum to said vacuum port to reconstitute the cervix as a treatment of preterm birth; and
  maintaining said vacuum by a valve connected to the vacuum port when a vacuum source is disconnected from the cervical cup.

15. The method according to claim 14, further comprising:
  reducing a downward pressure created by a presenting part of a fetus by the flange being tilted with respect to the axial axis of the body.

16. The method according to claim 14, further comprising:
  providing an amount of lift to a displacement of a downward pressure created by a presenting part of a fetus, by the flange formed by a curvature of the proximal end portion of the body so as to form a lip and extending the flange past the lip such that the curved end portion forming the flange radially extends away from the body.

17. The method according to claim 16, wherein the amount of lift to reduce the downward pressure created by the presenting part of the fetus is determined by a length of the lip of the cervical cup.

18. The method according to claim 14, further comprising:
  applying a medication to the cervix through a plurality of vents disposed on the flange by inserting a medicated ring disposed around an external surface of the body adjacent to the flange.

19. The method according to claim 14, wherein said inducing further comprises:
  improving a tissue durometer of the cervix;
  creating an edema; or
  increasing a cervical width, circumference, or length.

20. The method according to claim 14, further comprising:
  tilting the cervix by a curvature of said body with respect to a radial axis of the body.

* * * * *